United States Patent
Engmark et al.

[11] Patent Number: 5,637,417
[45] Date of Patent: Jun. 10, 1997

[54] QUICK CHANGE BATTERY DRAWER FOR EXTERNAL ELECTRICAL STIMULATOR

[75] Inventors: David B. Engmark, Bethel; Mark E. Jacoby, Minneapolis, both of Minn.

[73] Assignee: Medtronic, Inc., Minneapolis, Minn.

[21] Appl. No.: 554,882

[22] Filed: Nov. 7, 1995

[51] Int. Cl.$^6$ .................................................. H01M 2/10
[52] U.S. Cl. .................. 429/97; 429/96; 429/98; 429/100; 439/500; 607/9; 607/33
[58] Field of Search .................. 429/97, 96, 98–100; 439/500; 607/9, 33

[56] References Cited

U.S. PATENT DOCUMENTS

| | | | |
|---|---|---|---|
| 4,146,682 | 3/1979 | Nakao | 429/97 |
| 4,931,369 | 6/1990 | Hardt et al. | 429/98 |
| 5,103,216 | 4/1992 | Sisselman | 340/693 |
| 5,213,913 | 5/1993 | Anthony et al. | 429/97 |
| 5,224,870 | 7/1993 | Weaver et al. | 429/97 |
| 5,225,293 | 7/1993 | Mitchell et al. | 429/97 |
| 5,257,315 | 10/1993 | Haertl et al. | 381/68.6 |
| 5,265,168 | 11/1993 | Schiess et al. | 381/69 |
| 5,280,273 | 1/1994 | Goldstein | 340/632 |
| 5,410,141 | 4/1995 | Koenck et al. | 235/472 |
| 5,413,499 | 5/1995 | Wright, Jr. et al. | 439/500 |

OTHER PUBLICATIONS

Medtronic® Model 5345 Technical Manual, published Nov., 1992, pp. 43 & 44.

*Primary Examiner*—T. Tung
*Attorney, Agent, or Firm*—Thomas F. Woods; Harold R. Patton; Reed A. Duthler

[57] ABSTRACT

Disclosed is a quick change battery drawer for rapidly substituting a fresh battery for an exhausted battery in the battery drawer of an external, battery powered therapeutic electrical stimulator while the stimulator continues to emit electrical stimulation to treat a patient. A push button is normally biased outward and a release member latches the battery drawer in the latched position through the interaction of first catches on the battery drawer and second catches on the release member. The terminals of a battery loaded in the battery drawer bear against and compress spring terminals that thereby spring load the battery drawer with a bias force and assist in keeping the battery drawer latched. When the release button is depressed, the first and second catches are disengaged, and the bias force acts to eject the battery and battery drawer forcefully into an ejected position where the battery drawer is prevented from completely ejecting from the side opening. In the ejected position, the battery can be grasped and easily removed. A fresh battery is inserted into the battery drawer, and the user manually presses against the drawer end cap against the spring terminal bias force until the first and second catches are engaged. The spring loaded catches and the use of seals around the end cap and release button allows the tolerances between the battery drawer and the side opening, as well as internal drawer and release guides, to be relaxed, preventing any binding from slowing the action.

9 Claims, 9 Drawing Sheets

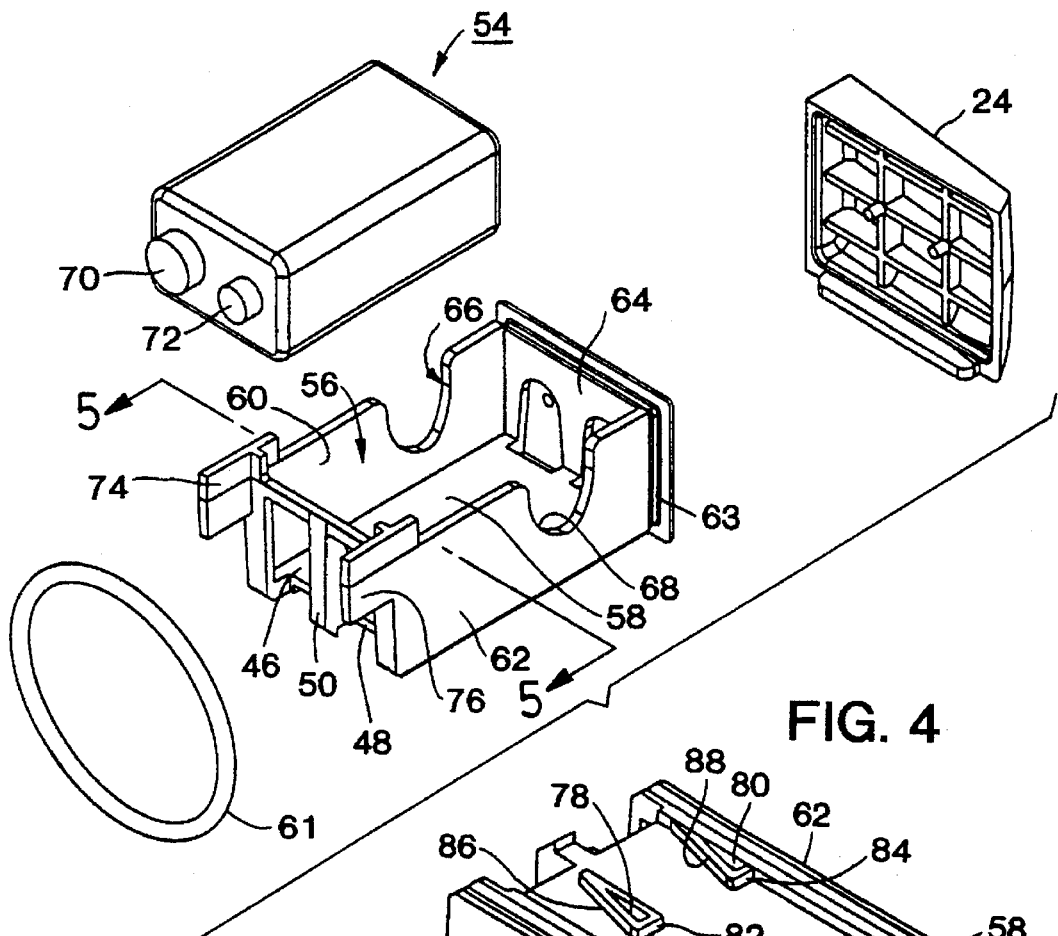
FIG. 3
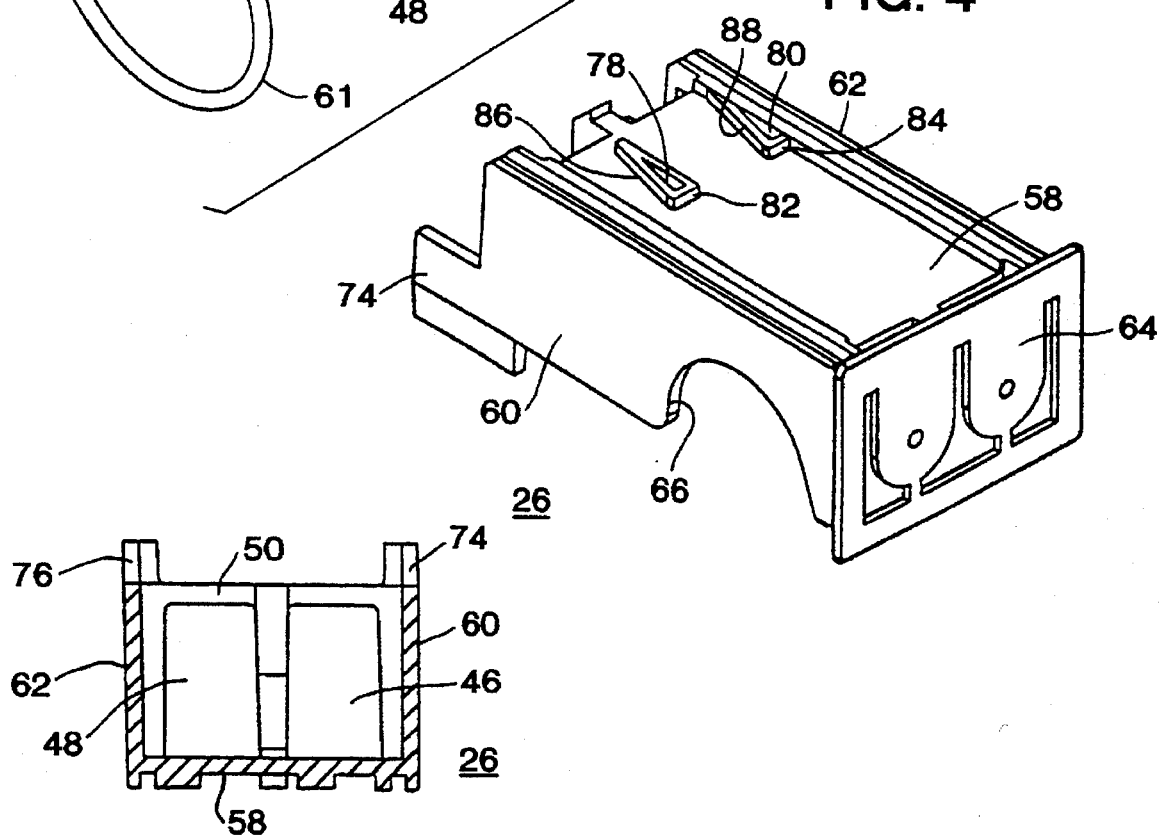
FIG. 4
FIG. 5

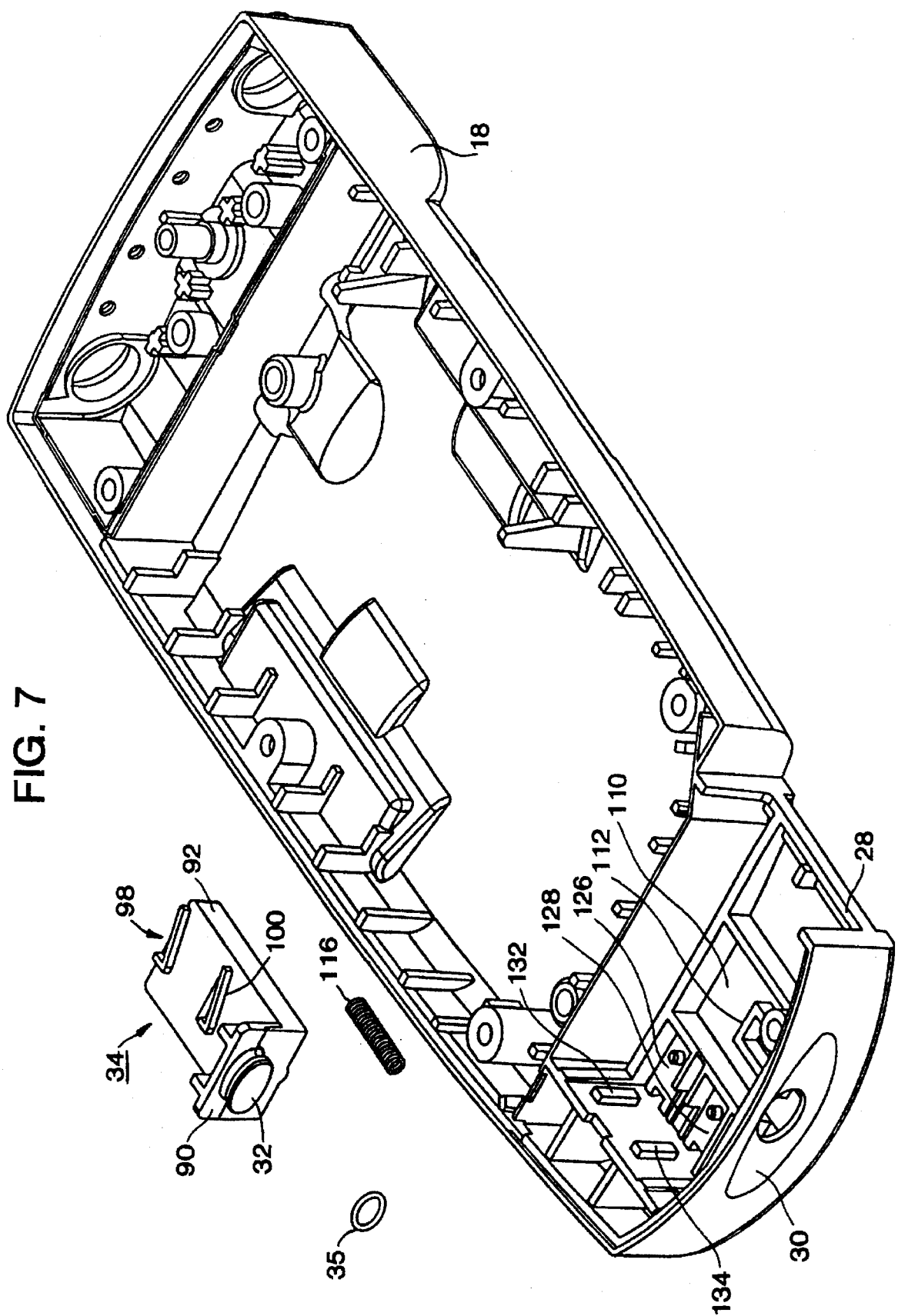

QUICK CHANGE BATTERY DRAWER FOR EXTERNAL ELECTRICAL STIMULATOR

CROSS-REFERENCE TO RELATED APPLICATION

Reference is hereby made to commonly assigned, co-pending U.S. Pat. application Ser. No. 08/554,887 filed on even date herewith for DUAL CHAMBER, MULTI-MODE CARDIAC PACEMAKER in the names of Richard Skoglund et at.

BACKGROUND OF THE INVENTION

1. Field of the Invention

The present invention relates to an external, battery powered therapeutic electrical stimulator, and more particularly to a quick change battery drawer for rapidly substituting a fresh battery for an exhausted battery while the stimulator continues to emit electrical stimulation to treat a patient.

2. Description of the Background Art

External, battery powered electrical stimulators, e.g. cardiac pacemakers and neurological stimulators, are widely used in the treatment of patients while the patients are ambulatory or confined in a medical facility. Portable, battery powered cardiac pacemakers may be strapped to a patient to provide a degree of freedom of movement even when the patient is confined and are used by ambulatory patients recovering from open heart surgery or otherwise requiring temporary pacing.

With external pacemakers typically used during a patient stay in a medical facility, the appropriate temporary lead system may be implanted in the patient, depending on the patient need, and the pulse generator may be switched to operate in one of the pacing modes prescribed by the attending physician. For example, during open heart surgery, temporary atrial and ventricular electrode beating leads may be implanted in the heart for post-operative dual chamber pacing during the recovery period and until the leads are removed. If one of the electrodes is dislodged from the heart, it may be necessary to switch to the appropriate single chamber pacing mode for the remaining electrode. In other cases, temporary single chamber pacing may be prescribed from the outset. Such typical external pacemaker pulse generators include the Medtronic® Model Nos. 5342, 5345 and 5346 external pacemakers, the Telectronics® Model 4553 external pacemaker, and the Pacesetter Systems, Inc. Model 3070 external pacemaker.

Such patients may be entirely or intermittently dependent on the temporary pacing therapy being delivered. After a period of pacing, it becomes necessary to replace the battery powering the pulse generator because the battery energy depletes. It is then necessary to quickly change the battery or substitute another pulse generator for the pulse generator being used. For patient's whose hearts are dependent on the continuous application of the pacing therapy, the loss of pacing during the replacement time may develop symptoms that are upsetting to the patient and the staff member making the battery change.

In the above-referenced Medtronic® external pacemaker pulse generators, the power supply circuit includes a capacitor for storing energy sufficient to maintain pacing for a brief period if the battery is removed. The electrical connection of the battery to the power supply circuit is maintained by contacts that are closed when the battery drawer is fully latched and opened as the drawer latch is released and the drawer is initially moved.

Full removal of the battery is effected by unlatching the battery drawer, manually pulling the drawer fully out of the drawer opening and retrieving the battery from the drawer. Due to manufacturing tolerances and aging of the plastic housing, the drawer sides and bottom may bind with the sides and bottom of the drawer opening into the housing, making it difficult to pull out the drawer, thereby increasing the replacement time.

SUMMARY OF THE INVENTION

It is therefore an object of the present invention to provide a quick change battery drawer for a medical electrical stimulator that is simple to operate and allows rapid removal and replacement of the battery.

In accordance with the present invention, an external medical stimulator having a housing for containing an electrical pulse generator circuit and supporting controls for controlling the operating parameters of the pulse generator, is provided with a quick release battery drawer operating system comprising: a battery drawer receiving chamber formed in the housing having a housing opening; a battery drawer operable in a latched position and an ejected position with respect to the housing opening providing a battery receptacle for receiving a battery having terminals oriented inwardly; first catch means formed in the battery drawer; a battery drawer releasing and engaging mechanism for effecting rapid movement of the battery drawer out of the opening in the housing to the ejected position, for engaging the battery drawer into the latched position upon depression of the battery drawer back into the opening, and for making an electrical connection of the at least one battery terminal with the electrical pulse generator circuit when the battery drawer is in the latched position, wherein the releasing and engaging mechanism further comprises: a release member supported in the housing and manually movable from an engaged position to a released position, the release member having second catch means for engaging the first catch means in the engaged position when the battery drawer is manually pushed into the housing to the closed position and for releasing the first catch means when manually moved to the released position; biasing means for biasing the release member to the engaged position; and at least one electrical spring terminal mounted to the housing and aligned to the inwardly oriented battery terminals and adapted to be compressed while making contact with a battery terminal when the battery drawer is in the latched position, whereby biasing force is released by the compressed spring terminal upon release of the release member to eject the battery drawer from the opening. The present invention advantageously provides the ability to quickly change the battery without loss of output pulses provided by the pulse generator

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 3 is an exploded perspective view of the battery drawer and the associated end cap and O-ring in relation to a battery;

FIG. 4 is a perspective bottom view of the battery drawer;

FIG. 5 is a cross-section end view of the battery drawer taken along lines 5—5;

FIG. 7 is an exploded perspective view of the pulse generator housing lower case, in part, and the components of the release mechanism in relation thereto;

DETAILED DESCRIPTION OF THE PREFERRED EMBODIMENT

Figure 1:
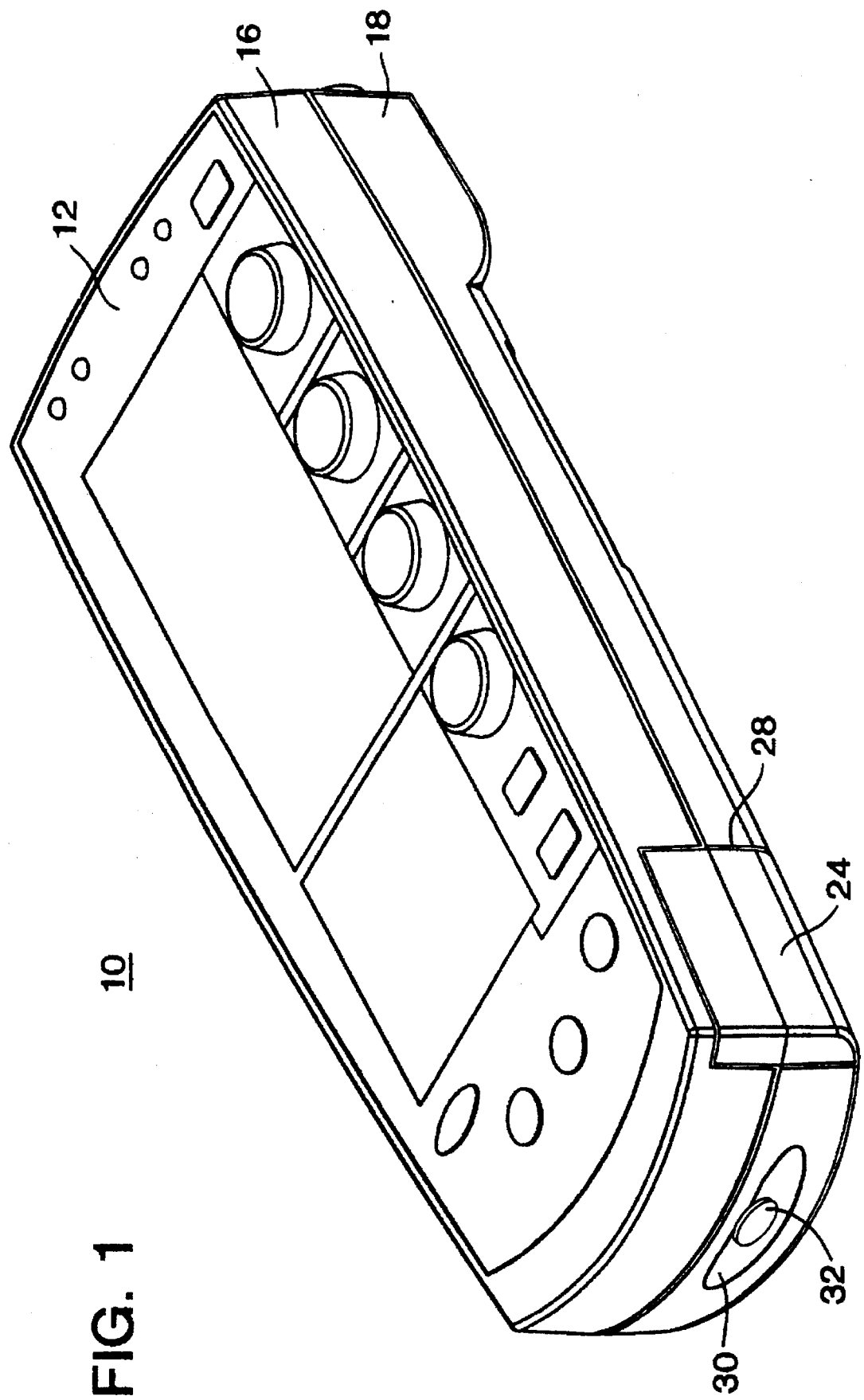
FIG. 1 is a perspective exterior view of the external pacemaker pulse generator housing in which the invention is preferably implemented.
Figure 2:
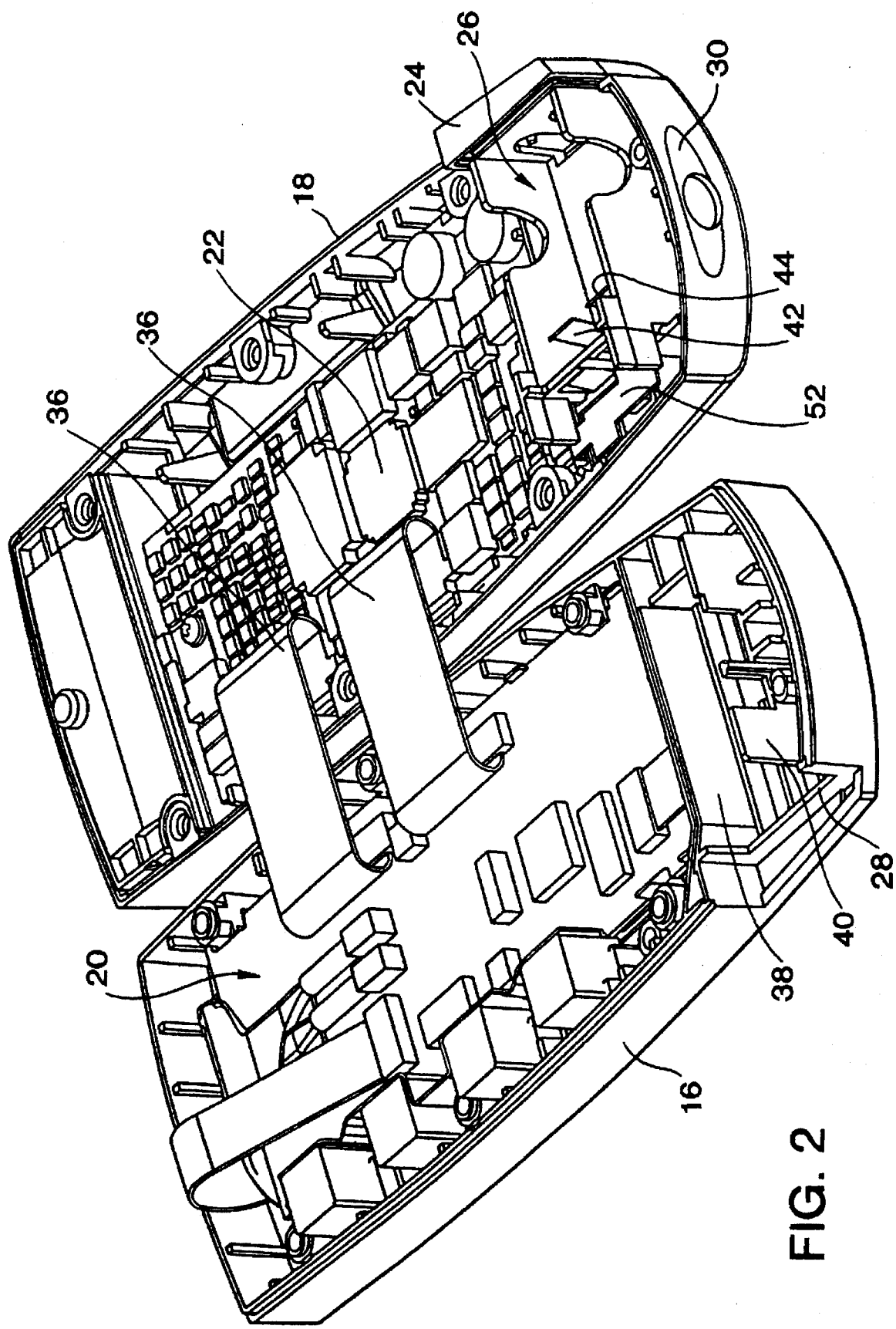
FIG. 2 is a perspective interior view of the upper and lower cases of the pulse generator housing of FIG. 1 showing the battery drawer and drawer release mechanism in part.

Turning to FIGS. 1 and 2 they depict, in exterior and interior views, the major components of a medical electrical stimulator 10, specifically a DDD pulse generator operating system with external controls and LCD panel displays for adjusting and displaying the operating mode and parameters of operation thereof, in which the present invention may be implemented. The stimulator 10 encases the pulse generator circuit within a housing 12 comprising an upper case 16 and a lower case 18. The interior of the upper case 16 supports a user interface module 20 including the LCD display panels, rotary dials and keys, shown in FIG. 1 exposed on or through the faceplate of the upper case 16, to be manipulated by the user to operate the pulse generator. The interior of the lower case 18 supports a circuit board 22 on which the pulse generator modules are assembled, the pulse generator modules including a timing and control module, an external communications module, a power supply module, a sense amp module, and a pacing output module. Flexible printed circuits 36 interconnect the pulse generator modules on circuit board 22 with the user interface module 20. The user interface module 20 and pulse generator modules mounted on printed circuit board 22, as well as the operation of the DDD pulse generator, form no part of the present invention, but are disclosed in detail in the above-referenced 08/554,877 application.

The battery drawer and release mechanism of the present invention is incorporated into the lower end of the housing 12 in both the upper and lower cases 16 and 18. As shown in FIG. 1, the rectangular decorative end cap 24 of the battery drawer 26 fits in a side opening 28 of housing 12 to move in and out between a latched position and an ejected position as described below. An opening and surrounding depression 30 is formed in the end of housing accommodating the release push button 32 of a release member 34 forming part of the release mechanism. As described below, the push button 32 is normally biased outward and the release member 34 latches the battery drawer 26 in the latched position through the interaction of first catches on the release member and second catches on the battery drawer 26.

The terminals of a battery loaded into the battery drawer 26 bear against and compress spring terminals that thereby spring load the battery drawer with a bias force and assist in keeping the battery drawer latched. When the release button 32 is depressed, the first and second catches are disengaged, and the bias force acts to eject the battery and battery drawer 26 forcefully into the ejected position. The battery drawer 26 is prevented from completely ejecting from the side opening 28. In the ejected position, the battery can be grasped and easily removed. A fresh battery is inserted into the battery drawer 26, and the user manually presses against the drawer end cap 24 against the spring bias force of the spring terminals until the first and second catches are engaged. The spring loaded catches and the use of seals around the end cap 24 and release button 32 allows the tolerances between the battery drawer 26 and the side opening 28, as well as internal drawer and release guides, to be relaxed, preventing any binding from slowing the action.

In FIG. 2, battery drawer side guides 38 and 40 are formed in the upper case 16 for guiding in and out movement of the battery drawer 26 in a battery drawer receiving chamber. In addition, the electrical spring terminals 42 and 44 for making contact with the battery terminals are depicted projecting through end openings 46 and 48 of the end wall 50 of the battery drawer 26. The spring terminals 42 and 44 are relaxed since a battery is not in the battery drawer 26. A battery flexible printed circuit 52 is also shown that interconnects the spring terminals 42 and 44 with the power supply module of the printed circuit board 22.

The configuration of the battery drawer 26 is shown in detail in FIGS. 3–5. The battery drawer confines the battery 54, preferably a standard 9.0 V battery, in a battery receptacle 56 formed of a base 58, elongated sidewalls 60, 62, end wall 50, and outer drawer end wall 64. Finger recesses 66 and 68 are formed in the elongated side walls 60, 62 to ease grasping of the battery 54. The end openings 46 and 48 of the end wall 50 are aligned to receive the spring terminals 42, 44 and are also aligned with the battery terminals 70 and 72, respectively, of battery 54. Extension ears 74 and 76 extend upwardly and rearwardly from the junction of the end wall 50 and the elongated side walls 60 and 62, respectively, to catch against guides in the upper case 16 to prevent the battery drawer 26 from being completely ejected from the side opening 28.

The decorative end cap 24 is also shown in relation to the outer drawer end wall 64 where it is attached. A battery drawer O-ring 61 is fitted into a drawer sealing groove 63 extending in a generally rectangular pattern around the periphery of the outer drawer end cap wall 64 to seal the periphery of the end wall 64 with the side opening 28 in the latched position of battery drawer 26 from dust and moisture infiltration.

The bottom view of battery drawer 26 of FIG. 4 shows a pair of first catches 78, 80 each formed as triangular bosses from the lower surface of drawer base 58. The triangular shaped first catches 78 and 80 have first engage surfaces 82 and 84, respectively, parallel to the end wall 50 and first cam surfaces 86 and 88, respectively, extending longitudinally at an angle to the side walls 60, 62.

Figure 9:
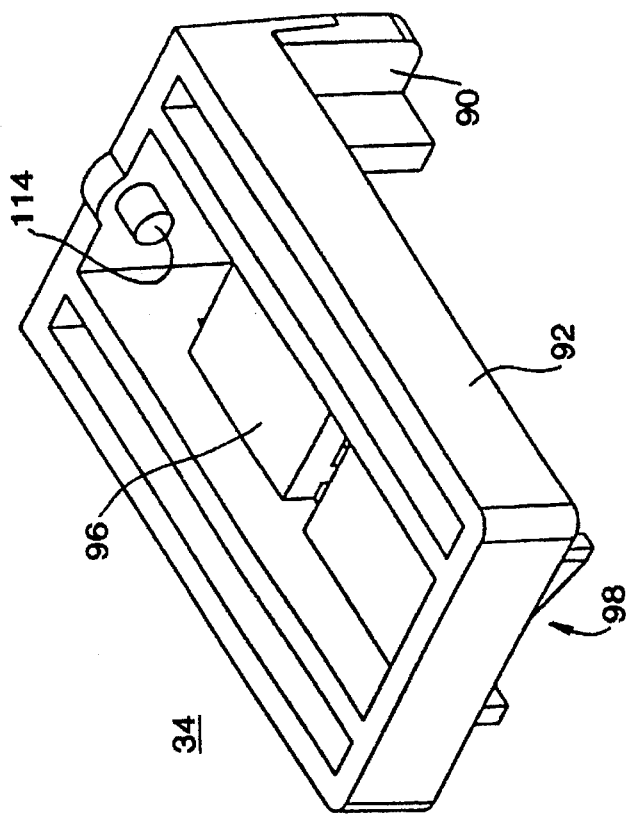
FIG. 9 is a perspective bottom view of the release member of the release mechanism.
Figure 8:
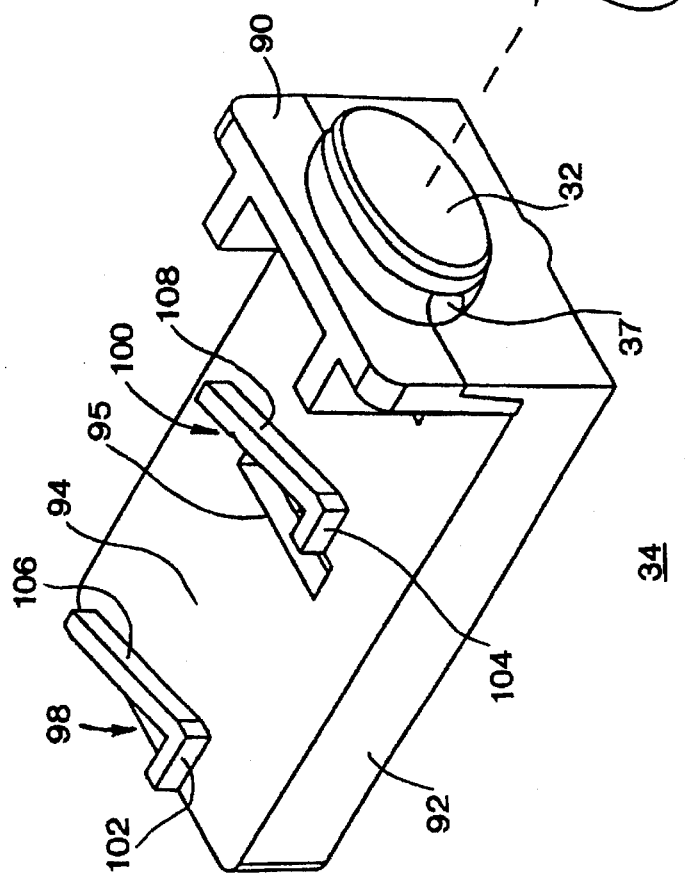
FIG. 8 is an exploded perspective view of the release member and an associated release member O-ring of the release mechanism.
Figure 11:
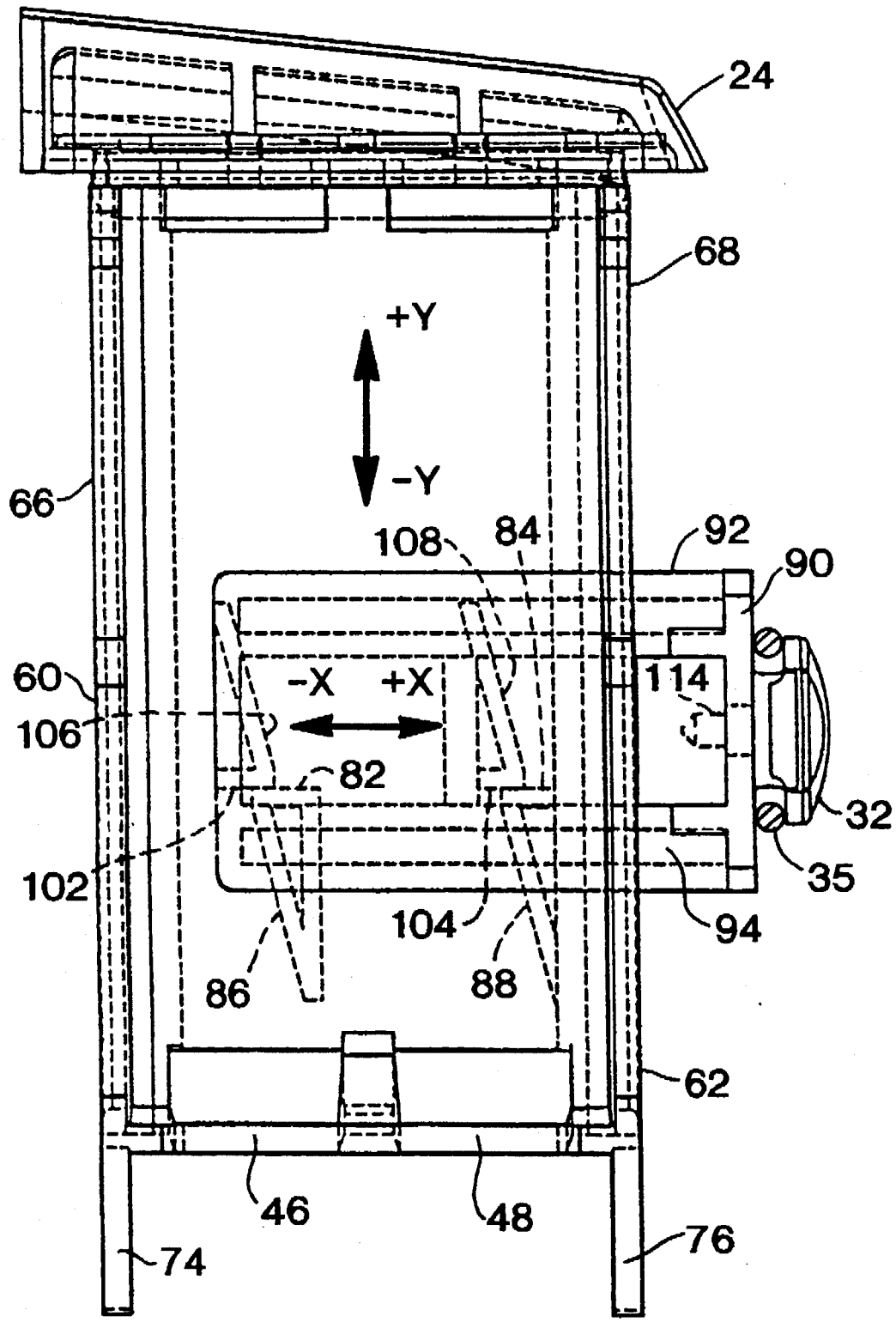
FIG. 11 is a plan view of the assembled battery drawer in relation to the release mechanism in the drawer latched position.
Figure 12:
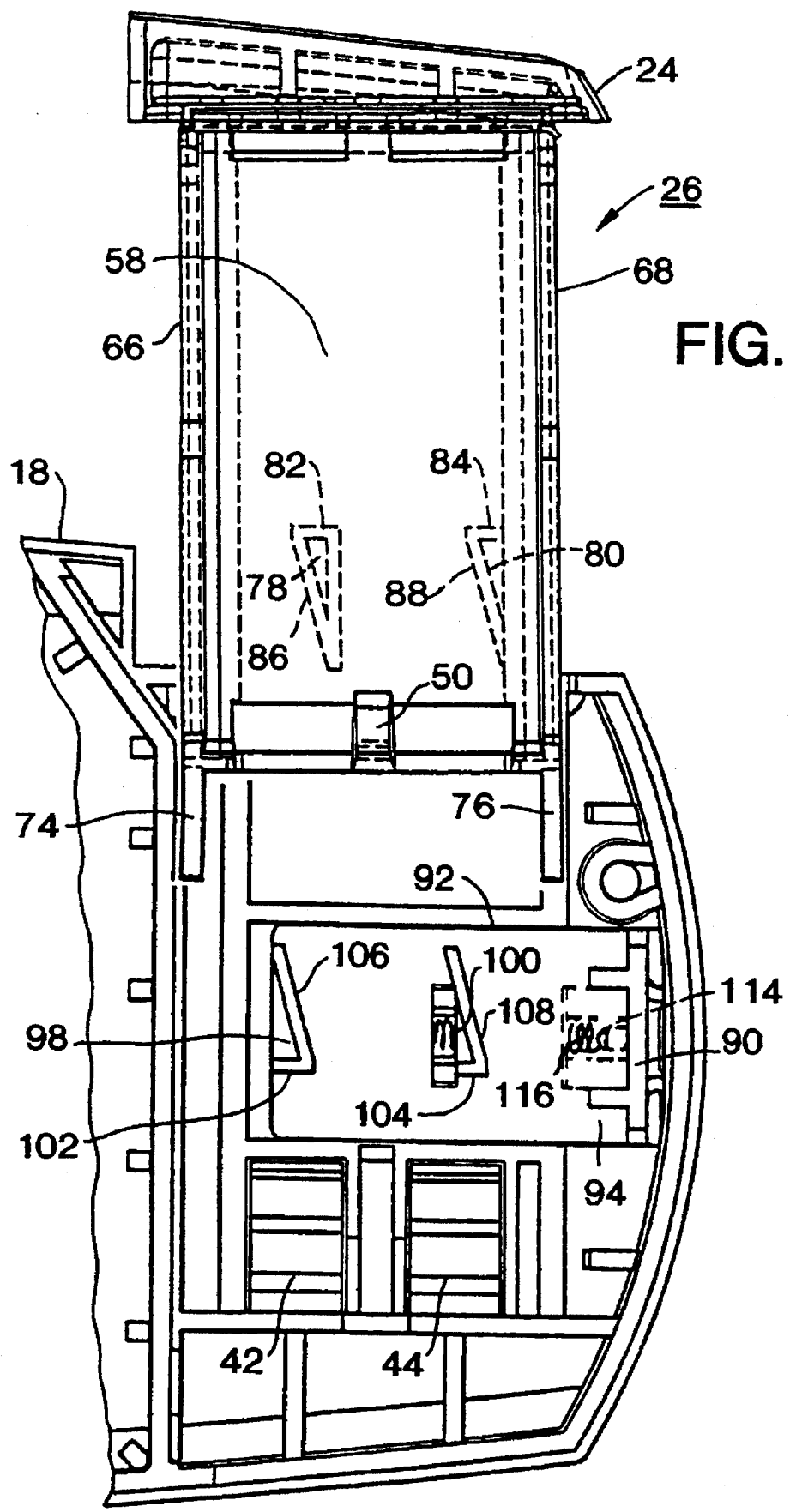
FIG. 12 is a plan view of the assembled battery drawer in relation to the release mechanism in the drawer ejected position.

Turning to FIGS. 8 and 9, the release member 34 and an associated release button O-ring 35 of the release mechanism are depicted in top and bottom perspective views. The release member 34 has an end plate 90 supporting the release button 32 and a generally rectangular shaped extension 92 therefrom having an upper surface 94 and a lower elongated recess 96. A pair of second catches 98, 100 extend as triangular bosses from the upper surface 94. The triangular shaped, second catches 98 and 100 have second engage surfaces 102 and 104, respectively, extending parallel to the end wall 50 (as shown in FIGS. 11 and 12) and second cam surfaces 106 and 108, respectively, extending longitudinally at an angle to the side walls 60, 62 (as shown in FIGS. 11 and 12).

The elongated extension 92 fits within a case recess 110 in the lower case 18 and over the release guide 112 shown in FIG. 7 such that the release guide 112 fits within the elongated recess 96. The end plate 90 is formed with a spring retention post 114 extending toward the elongated recess 96 as shown in FIG. 9. The elongated recess 96 and the release guide 112 are shaped to receive and compress the coil spring 116, also depicted in the exploded perspective view of FIG. 7. The compression of the coil spring 116 against the fixed end of the release guide 112 and the retention post 114 causes it to apply force against the end plate 90 of the movable release member 34 and bias the release button outward of the opening in the end of lower case 18. A spring access opening 95 extends between the upper surface 94 and the lower elongated recess 96, which may be used in assembling the coil spring 116 within the elongated recess 96 and the release guide 112 when the release member 34 is fitted into the case recess 110.

Figure 10:
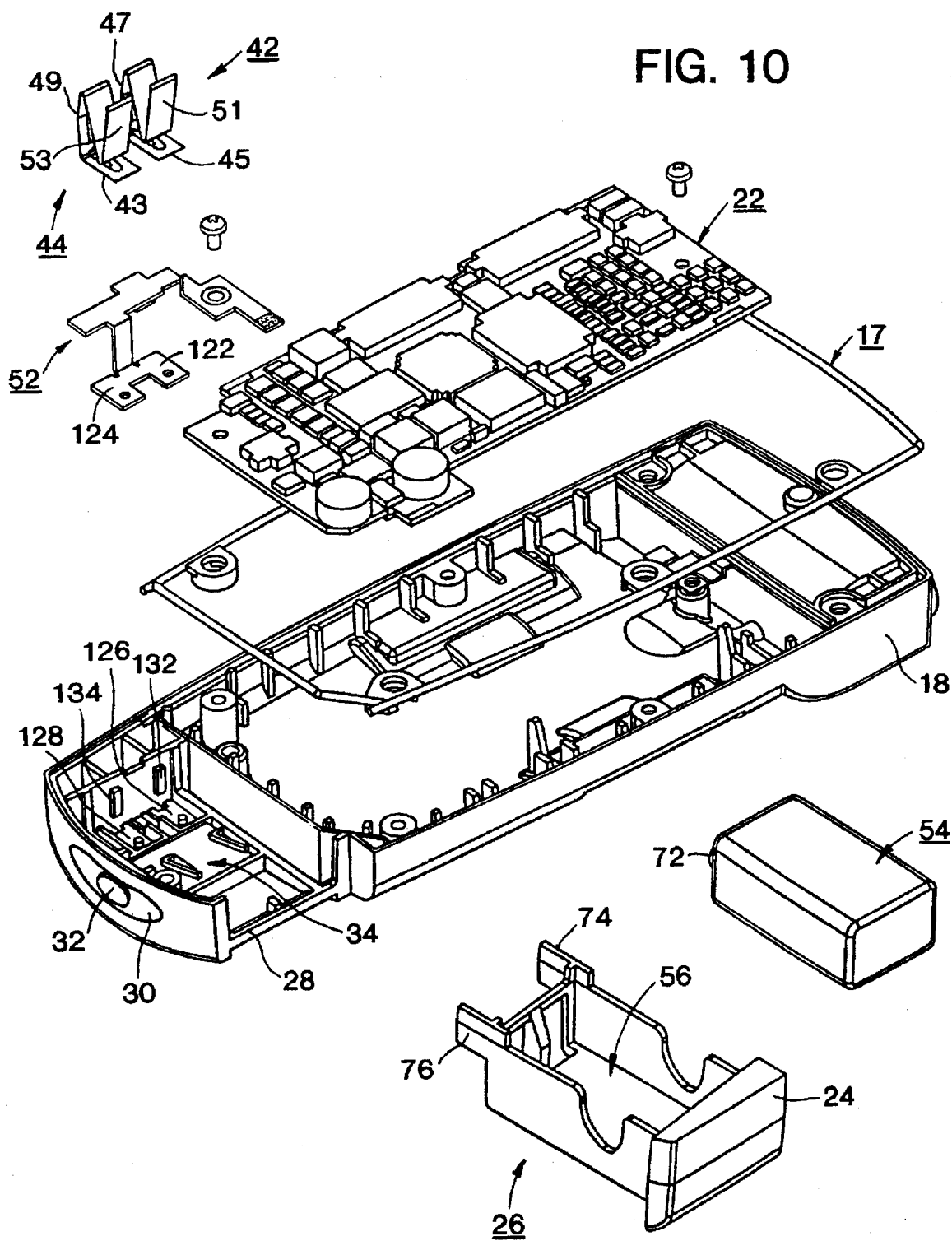
FIG. 10 is an exploded perspective view of the pulse generator housing lower case, in part, and the components of the battery drawer and spring biased battery contacts in relation thereto.

The release button O-ring 35 is fitted into an oval sealing groove 37 around the oval release button 32. When the release member is positioned, the O-ring 35 is inside the lower case 18 and provides a dust and moisture seal of the space between the release button 32 and the end opening in depression 30. FIG. 10 depicts the release member 34 positioned in the recess 110 with the coil spring 116 trapped below it between the retention post 114 and the release guide 112.

Figure 6:
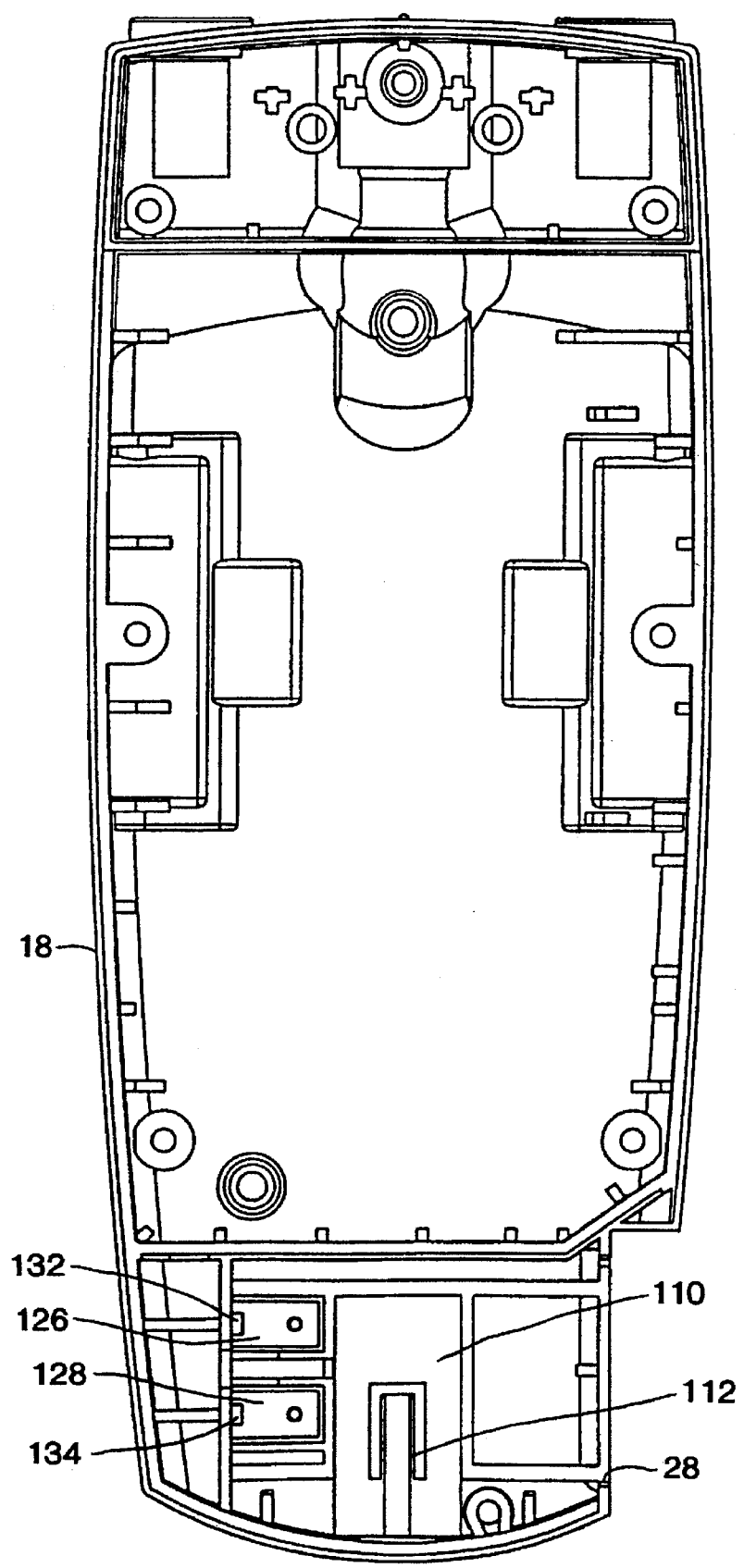
FIG. 6 is a plan view of the interior of the pulse generator housing lower case showing where the components of the battery release mechanism and battery drawer are fitted.

FIG. 10 also shows the alignment of the battery drawer 26 and the battery 54 in relation to the lower case 18, and the orientation of the electrical components for making electrical contact between the battery terminals and the power supply module on printed circuit board 22. The battery flexible printed circuit 52 has branching circuit contacts 122 and 124 that fit into contact recesses 126 and 128 (also shown in FIG. 6). Openings in branching circuit contacts 126 and 128 fit over upwardly extending pins in contact recesses 126 and 128. Horizontal end extensions or feet 43 and 45, respectively, of the spring terminals 42 and 44 fit over the branching circuit contacts 122 and 124, respectively, and the pins in the contact recesses 126 and 128, respectively, and make electrical connection therewith. The battery flexible printed circuit 52 is connected to the power supply module, and the printed circuit board 22 is mounted in the lower case 18.

As shown in FIG. 10, the spring terminals 42 and 44 also have vertically extending sections 47 and 49, respectively, with holes formed therein that fit over and are staked by posts 132 and 134, respectively. When so attached, the folded, V-shaped leaf spring sections 51 and 53 of spring terminals 42 and 44, respectively, extend through the end openings 46 and 48 of the inner end wall 50 of battery drawer 26 in a non-interfering manner.

The battery drawer 26 is fitted over the release member 34 and between the battery drawer side guides 38 and 40 of the upper case 16. The electrical connections and assemblies shown in FIG. 2 are completed and the upper and lower cases 16 and 18 are connected together, employing a sealing gasket 17. The extension ears 74 and 76 then entrap the battery drawer 26 within the side opening 28 and prevent it from falling out in the ejected position.

The latched and ejected positions and the interactions of the battery drawer 26 and the release mechanism are shown schematically in FIGS. 11 and 12. FIG. 11 depicts the battery drawer latched position wherein the first engage surfaces 82, 84 bear against the second engage surfaces 102, 104, respectively. In the latched position, the leaf spring sections 51 and 53 of spring terminals 42, 44, respectively, are compressed and bear against the terminals of a battery (not shown) to make a secure electrical contact. At the same time, the spring force of the compressed coil spring 116 biases release member 34 in the direction of arrow +X. The combination of leaf and coil spring forces maintains the latched drawer position against external shock or vibration forces, e.g. the dropping of the pulse generator.

When the release button 32 is depressed in the direction −X to compress the coil spring 116, the second engage surfaces 102, 104 slide past the first engage surfaces 82, 84, respectively, to a release point where the first catches 78, 80, respectively, are released. The bias forces of the spring terminals 42, 44 are suddenly released and act to eject the battery and battery drawer 26 forcefully in the +Y direction into the ejected position of FIG. 12.

In the ejected position of FIG. 12, the battery can be grasped through the finger recesses 66 and 68, removed and replaced with a fresh battery. In certain pulse generators, the power supply module is able to determine the polarity of the battery terminals 70, 72 after contact is made and adjust to the order. In other pulse generators, it is necessary to replace the battery with the proper orientation of battery terminals 70, 72 to the battery receptacle 56 and the spring terminals 42, 44. In either case, the battery may be rapidly replaced, and electrical contact re-established upon closure of the battery drawer 26 into the latched position.

The battery drawer 26 is moved in the −Y direction to the latched position by pressing the decorative end cap 24 so that the first cam surfaces 86, 88 slide along the second cam surfaces 106, 108, respectively. The sliding movement causes the release member extension 92 to move in the −X direction until the latched position is reached, and the second engage surfaces 102, 104 are aligned with the first engage surfaces 82, 84, respectively. At that point, the second engage surfaces 102, 104 suddenly slide along the first engage surfaces 82, 84, respectively, in the +X direction under the force of coil spring 116, and the battery drawer 26 is securely latched.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

| PARTS LIST FOR FIGS. 1–12 |
| --- |
| medical electrical stimulator 10 |
| external housing 12 |
| upper case 16 |
| lower case 18 |

-continued

PARTS LIST FOR FIGS. 1–12 user interface module 20
printed circuit board 22
decorative end cap 24
battery drawer 26
side opening 28
end opening and depression 30
release push button 32
release member 34
release button O-ring 35
flexible printed circuits 36
sealing groove 37
battery drawer side guides 38, 40
spring terminals 42, 44
horizontal end extensions or feet 43, 45
end openings 46, 48
vertically extending sections 47, 49
battery drawer end wall 50
V-shaped leaf spring sections 51, 53
battery flexible printed circuit 52
battery 54
battery receptacle 56
drawer base 58
elongated drawer side walls 60, 62
battery drawer O-ring 61
drawer sealing groove 63
drawer end cap wall 64
finger recesses 66, 68
battery terminals 70, 72
extension ears 74, 76
fist catches 78, 80
first engage surfaces 82, 84
first cam surfaces 86, 88
end plate 90
extension 92
upper surface 94
access opening 95
lower elongated recess 96
second catches 98, 100
second engage surfaces 102, 104
second cam surfaces 106, 108
recess 110
release guide 112
spring retention post 1 14
coil spring 116
branching contacts 122, 124
contact recesses 126, 128
posts 132 and 134

We claim:

1. In an external medical stimulator having a housing for containing an electrical pulse generator circuit and supporting controls for controlling the operating parameters of said pulse generator, a quick release battery drawer operating system, comprising:

a battery drawer receiving chamber formed in said housing having a housing opening;

a battery drawer operable in a latched position and an ejected position with respect to said housing opening providing a battery receptacle for receiving a battery having at least one battery terminal oriented inwardly; and a battery drawer releasing and engaging mechanism for effecting rapid movement of said battery drawer out of said opening in said housing to said ejected position, for engaging said battery drawer into said latched position upon depression of said battery drawer back into said opening, and for making an electrical connection of said at least one battery terminal with said electrical pulse generator circuit when said battery drawer is in said latched position, wherein said releasing and engaging mechanism further comprises:

a release member supported in said housing and manually movable from an engaged position to a released position; and at least one electrical spring terminal attached to said housing and aligned in respect of said inwardly oriented battery terminal such that the spring terminal is compressed while establishing electrical and mechanical contact with the at least one battery terminal when said battery drawer is in said latched position, such that biasing force is released by said compressed spring terminal upon release of said release member to eject said battery drawer from said opening and into said ejected position.

2. The external medical stimulator of claim 1 wherein said medical stimulator is a cardiac pacemaker.

3. In an external medical stimulator having a housing for containing an electrical pulse generator circuit and supporting controls for controlling the operating parameters of said pulse generator, a quick release battery drawer operating system, comprising:

a battery drawer receiving chamber formed in said housing having a housing opening;

a battery drawer operable in a closed latched position and an open ejected position with respect to said housing opening providing a battery receptacle for receiving a battery having at least one terminal oriented inwardly;

first catch means formed in said battery drawer;

a battery drawer releasing and engaging mechanism for effecting rapid movement of said battery drawer out of said opening in said housing to said ejected position, for engaging said battery drawer into said latched position upon depression of said battery drawer back into said opening, and for making an electrical connection of said at least one battery terminal with said electrical pulse generator circuit when said battery drawer is in said latched position, wherein said releasing and engaging mechanism further comprises:

a release member supported in said housing and manually movable from an engaged position to a released position, said release member having second catch means for engaging said first catch means in said engaged position when said battery drawer is manually pushed into said housing to said closed position and for releasing said first catch means when manually moved to said released position;

biasing means for biasing said release member to said engaged position; and at least one electrical spring terminal attached to said housing and aligned in respect of said inwardly oriented battery terminal such that the spring terminal is compressed while establishing electrical and mechanical contact with the at least one battery terminal when said battery drawer is in said latched position, such that biasing force is released by said compressed spring terminal upon release of said release member to eject said battery drawer from said opening.

4. The external medical stimulator of claim 3 wherein said medical stimulator is a cardiac pacemaker.

5. In an external medical stimulator having a housing for containing an electrical pulse generator circuit and supporting controls for controlling the operating parameters of said pulse generator, a quick release battery drawer operating system, comprising:

a battery drawer operable in a closed latched position and an ejected position with respect to an opening in said housing and further comprising:

a base connecting a pair of parallel drawer sidewalls, an outer drawer face end wall, and an inner drawer end wall providing a battery receptacle for receiving a battery having at least one terminal oriented toward said inner drawer end wall;

at least one end opening formed in said inner drawer end wall aligned with the at least one battery terminal;

first catch means formed in said base of said battery drawer having a first cam surface;

a battery drawer releasing and engaging mechanism for effecting rapid movement of said battery drawer out of said opening in said housing to said ejected position, for engaging said battery drawer into said latched position upon depression of said battery drawer back into said opening, and for establishing electrical connection between said at least one battery terminal and said electrical pulse generator circuit when said battery drawer is in said latched position, wherein said releasing and engaging mechanism comprises:

a release member supported in said housing and manually movable from an engaged position to a released position, said release member having second catch means for engaging said first catch means when said battery drawer is manually pushed into said housing to said closed position and a second cam surface aligned to bear against said first cam surface as said battery drawer is moved into and out of said closed position;

biasing means for biasing said release member to said engaged position; and at least one electrical spring terminal attached to said housing and aligned in respect of said at least one end opening such that the spring terminal is compressed while establishing electrical and mechanical contact with said at least one battery terminal when said battery drawer is in said latched position, such that biasing force is released by said compressed spring terminal upon release of said release member to eject said battery drawer from said opening.

6. The external medical stimulator of claim 5 wherein said medical stimulator is a cardiac pacemaker.

7. The external medical stimulator of claim 5 wherein said biasing means comprises a coil spring.

8. An external medical stimulator, comprising:

(a) an external pulse generator circuit;

(b) controls for controlling the operating parameters of the pulse generator circuit;

(c) a housing having an interior portion and an exterior surface, the pulse generator circuit being disposed within the interior portion, the exterior surface supporting the controls, the housing having a battery drawer receiving chamber formed in the interior portion thereof, the chamber being defined approximately by at least a rear wall, a side wall, and a bottom wall, the housing further having a battery drawer opening formed in the exterior surface thereof and contiguous with the chamber, the opening opposing the rear wall;

(d) a quick release battery drawer conforming approximately to the volume and shape of the chamber, the drawer fitting within the chamber through the opening and being supported by the bottom wall when in a first closed, latched position, the drawer having a receptacle disposed therein for receiving a standard nine-Volt battery having its terminals oriented inwardly towards the rear wall, the drawer being in a second open position when ejected from the chamber, the drawer having a first catch formed thereon;

(e) an engaging mechanism having a second catch formed thereon, the engaging mechanism being attached to the housing, the position of the first catch corresponding to the position of the second catch such that the first catch engages the second catch and the battery drawer is held in the first latched position when the drawer is pushed sufficiently far into the chamber;

(f) a manually moveable release mechanism attached to the housing, a portion of the release mechanism engaging or forming a portion of the engaging mechanism, wherein as the release mechanism is manually moved to a released position the second catch disengages from the first catch and the battery drawer is ejected into the second open position, and (g) at least one compressible electrical spring terminal having first and second ends electrically connected to one another, the first end being attached to the housing and electrically connected to the pulse generator circuit, the second end engaging and establishing electrical contact with one terminal of the nine-Volt battery as the battery drawer is moved from the second open position to the first latched position, the spring terminal being compressed as the battery drawer is moved from the second open position to the first latched position, the compressed spring terminal providing a biasing force for ejecting the battery drawer into the second open position when the release mechanism is moved into the released position.

9. An external medical stimulator, comprising:

(a) circuit means for generating external pulses;

(b) means for controlling the operating parameters of the circuit means;

(c) means for housing having an interior portion and an exterior surface, the circuit means being disposed within the interior portion, the exterior surface supporting the means for controlling, the housing means having a battery drawer receiving chamber formed in the interior portion thereof, the chamber being defined approximately by at least a rear wall, a side wall, and a bottom wall, the housing means further having a battery drawer opening formed in the exterior surface thereof and contiguous with the chamber, the opening opposing the rear wall;

(d) means for a quick release battery drawer conforming approximately to the volume and shape of the chamber, the drawer means fitting within the chamber through the opening and being supported by the bottom wall when in a first closed, latched position, the drawer means having a receptacle disposed therein for receiving a standard nine-Volt battery having its terminals oriented inwardly towards the rear wall, the drawer means being in a second open position when ejected from the chamber, the drawer means having a first means for catching formed thereon;

(e) a means for engaging having a second means for catching formed thereon, the engaging means being attached to the housing means, the position of the first catching means corresponding to the position of the second catching means such that the first catching means engages the second catching means and the drawer means is held in the first latched position when the drawer means is pushed sufficiently far into the chamber;

(f) a manually moveable means for releasing attached to the housing means, a portion of the releasing means engaging or forming a portion of the engaging means, wherein as the releasing means is manually moved to a released position the second catching means disengages from the first catching means and the drawer means is ejected into the second open position, and (g) at least one spring terminal means for establishing electrical connection, the spring terminal means being compressible and having first and second ends electrically connected to one another, the first end being attached to the housing and electrically connected to the circuit means, the second end engaging and establishing electrical contact with one terminal of the nine-Volt battery as the drawer means is moved from the second open position to the first latched position, the spring terminal means being compressed as the drawer means is moved from the second open position to the first latched position, the compressed spring terminal means providing a biasing force for ejecting the battery drawer means into the second open position when the releasing means is moved into the released position.

* * * * *

UNITED STATES PATENT AND TRADEMARK OFFICE
CERTIFICATE OF CORRECTION

PATENT NO. : 5,637,417

DATED: June 10, 1997

INVENTOR(S): Engmark et al.

It is certified that error appears in the above-identified patent and that said Letters Patent is hereby corrected as shown below:

Col. 1, Line 37: delete "beating" insert-- bearing --.

Col. 1, Line 10: "et at." should be "et al."

Col. 6, Line 66: Between line 65 & 67 insert "case sealing gasket 17"

Col. 7, Line 39: "1 14" should be "114"

Signed and Sealed this

Third Day of August, 1999

Attest:

Q. TODD DICKINSON

Attesting Officer     Acting Commissioner of Patents and Trademarks